Figure 1A:
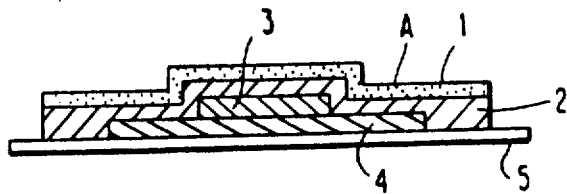

United States Patent [19]

Shikinami et al.

[11] Patent Number: 4,997,656
[45] Date of Patent: Mar. 5, 1991

[54] ADHESIVE FOR PERCUTANEOUS ADMINISTRATION

[75] Inventors: Yasuo Shikinami; Seiei Sasatani, both of Osaka, Japan

[73] Assignees: Takiron Co., Ltd.; Ono Pharmaceutical Co., Ltd., both of Osaka, Japan

[21] Appl. No.: 356,618

[22] Filed: May 23, 1989

Related U.S. Application Data

[63] Continuation of Ser. No. 49,496, May 14, 1987, abandoned.

[30] Foreign Application Priority Data

May 14, 1986 [JP] Japan ............................... 61-108633
Apr. 17, 1987 [JP] Japan ............................... 62-83772

[51] Int. Cl.⁵ .......................................... A61M 37/00
[52] U.S. Cl. ............................... 424/448; 424/449
[58] Field of Search ................. 424/448, 446, 78, 79

[56] References Cited

U.S. PATENT DOCUMENTS 4,202,880  5/1980  Fildes et al. ........................ 424/78
4,235,988  11/1980 Fildes et al. ........................ 528/79
4,762,899  8/1988  Shikinami ........................... 528/49

FOREIGN PATENT DOCUMENTS 1551563  5/1978  United Kingdom .
1551620  8/1979  United Kingdom .

Primary Examiner—Thurman Page
Assistant Examiner—L. Horne
Attorney, Agent, or Firm—Sughrue, Mion, Zinn, Macpeak & Seas

[57] ABSTRACT

An adhesive for percutaneous administration having a drug-containing layer composed of a base component mainly comprising a heat-sensitive and water-sensitive amphiphilic polymer and a drug incorporated in the base component. The amphiphilic compound has a characteristic hydrophobicity-hydrophilicity tapered structure, and a variety of liquid or solid or lipophilic (hydrophobic) or hydrophilic drugs of a broad range can stably be dissolved or dispersed therein. The drug in the drug-containing layer remains stable without being released or diffused while the adhesives are stored, and upon application to the skin, the drug is gradually released and diffused into the skin with high availability in a specifically controlled pattern. The present adhesive is especially advantageous for endermic presentation of a slight amount of a substance of high physiological activity which is unstable and is easily decomposed by heat or water.

13 Claims, 2 Drawing Sheets

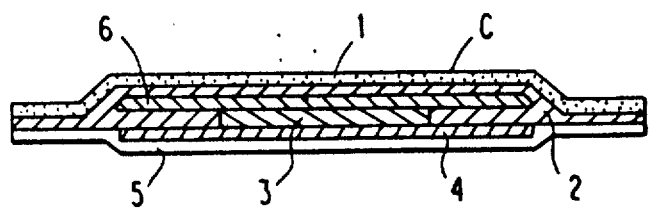
FIG.3
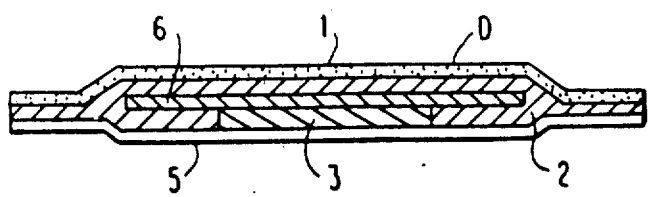
FIG.4
FIG.5
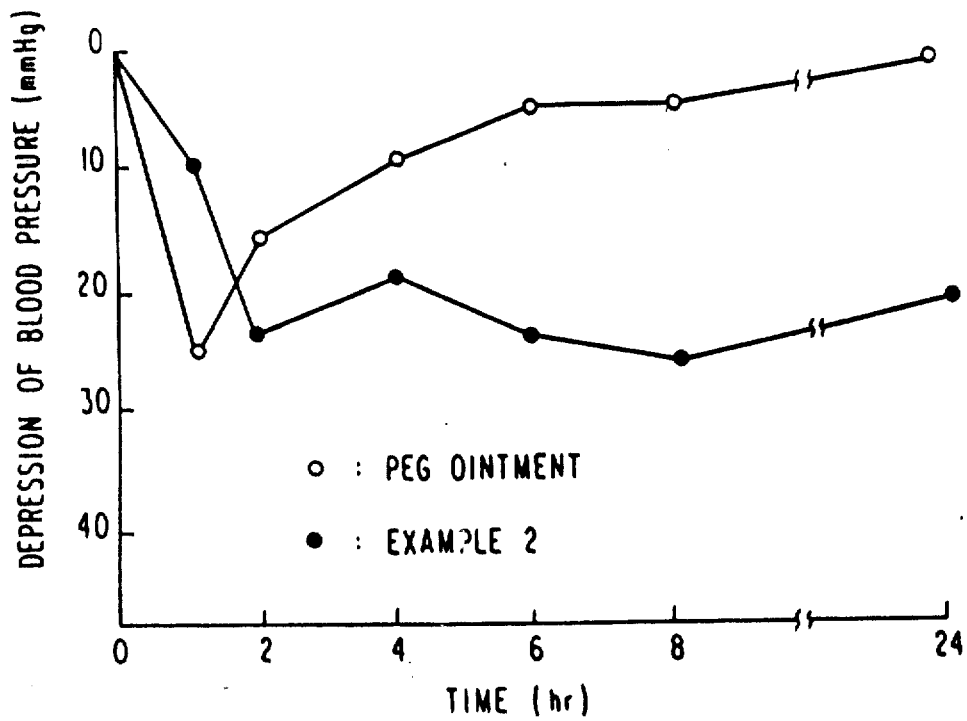

ADHESIVE FOR PERCUTANEOUS ADMINISTRATION

This is a continuation-in-part of application Ser. No. 07/049,496, filed May 14, 1987, now abandoned.

FIELD OF THE INVENTION

The present invention relates to a controlled release preparation for percutaneous administration capable of being adapted for various kinds of pharmaceutical substances of a broad range. More precisely, the present invention provides an adhesive for percutaneous administration where the main base component of a drug-containing layer, comprising a multi-block copolymer of an amphiphilic segment polyurethane which is solid at normal temperature and which has both heat-sensitivity and water-sensitivity, has a specific drug-releasing mechanism because of the action of the amphiphilic block copolymer, and the adhesive for percutaneous administration have a high availability with a pertinently controlled drug-releasing pattern and further have an excellent preservation-stability. By the use of the adhesive for percutaneous administration of this kind, even a slight amount of a substance which has a high physiological activity but is apt to be decomposed extremely easily can transdermically be administered through the skin, the substance having heretofore been considered most difficult to be used for percutaneous administration because of the rapid decomposition thereof.

BACKGROUND OF THE INVENTION

Percutaneous absorbents have heretofore been known in various forms including ointment (creams, gels), solid plaster agents, tape agents, cataplasm agents, liniment agents, lotion agents, aerosol agents, etc. For local application, various drugs can be delivered by means of such percutaneous absorbents, including (1) antihistamines, steriods, non-steroid series anti-inflammatory agents, antipruritics, (2) medicines for suppurative skin diseases or for parasitic skin diseases, such as sulfa drugs, antibiotics, etc., (3) other pharmaceutical substances such as skin-softening agents, medicines for leukoplakia vulgaris, etc.

Recently, the transdermal therapeutic system (TTS) has been studied extensively, using preparations for general systemic application, in order to improve the therapeutic effect by maintaining the concentration of a drug in the blood-stream for a long period of time, reducing any harmful side effects occurring due to the pathway of the drug administered, and improving the compliance of drugs. Various kinds of preparations of this type have recently been developed, including nitroglycerin, isosorbitol nitrate, clonidine, scopolamine, etc.

More recently, attention has turned to transdermal systems for medicines that require the controlled release of an active component having a high activity even in a slight amount, poor stability in vivo, and a narrow safety margin (for example, digoxin, lidocaine, quinidine, theophylline, etc.), as drugs for percutaneous administration, are being investigated in this technical field.

Heretofore, natural rubber series substances, synthetic rubber series substances, acrylic resin series substances, celluloses, polysaccharides, silicones or oily gels containing synthetic rubber-mineral oil, etc., as well as sodium acrylate or aqueous gels containing a water-soluble polymer (e.g., polyvinyl alcohol, etc.) and water have been utilized as base substances for drugs for percutaneous administration.

These polymer compounds are used in the base component or additives for a drug for percutaneous administration, either as constitutional components having physical and mechanical characteristics such as self-restorativity, adhesiveness, etc., in the form of a support for a pharmaceutical substance, or as functional components. Such functional component are typically polymers selected on account of the chemical characteristics of the monomer units themselves, chemical characteristics of the segment units of the chain structure and of the main chain and side chains of the polymer units, as well as the chemical interaction between the polymers themselves or the interaction between the polymer and the pharmaceutical component, additionally in the form of an aggregate of the polymer molecules In most embodiments of conventional percutaneous preparations, polymers are used essentially as constitutional components. Specifically, most polymers are used as a matrix for a drug to be transdermically absorbed, in conventional drug for percutaneous administration. Systems that are designed chiefly on the basis of functional components, in consideration of the interaction between the molecular structure of a polymer and a low molecular compound (drug), have not been as thoroughly investigated in the past. The present invention has been accomplished by molecular-planning of a base component which is extremely useful as a percutaneous absorbent. Polymeric agents capable of producing sustained release of a substance having high physiological activity are few. Japanese Patent Publication No. 9922/86 (corresponding to U.S. Pat. Nos. 4,202,880 and 4,235,988, British Patent No. 1,551,620, and Belgian Patent No. 861,788) relates to the combination of a prostaglandin derivative (sodium fluprostenol) as a substance having high physiological activity and a hydrophilic linear polyoxyalkylene/polyurethane block copolymer as a base component. However, this preparation has the disadvantage that the base component is not heat-sensitive. Japanese Patent Publication No. 9922/86 relates to agents for percutaneous administration and does not disclose an adhesive for percutaneous administration. The base component used in Japanese Patent Publication No. 9922/86 is composed of a block copolymer comprising a repeating unit of ABABAB ..., wherein A represents a hydrophilic part such as one or more polyoxyalkylene and B represents a hydrophobic part such as a diisocyanate and one or more hydroxy compound In addition, Japanese Patent Publication No. 9922/86 teaches that the polymer is dissolved in a solvent and the pharmaceutical substance is admixed and dispersed therein, and when the agent is used, a humor penetrates into the dispersion composition in order to form a diffusing pathway through the body tissue which is kept in contact with the dispersion composition, and as a result, a durable release of the physiological active substance from the agent into the body tissue is attained through the diffusing pathway. Japanese Patent Publication No. 9922/86 discloses a polymer having both hydrophilic and hydrophobic parts, but fails to teach or suggest the importance of the interaction between the polymer and the pharmaceutical substance or the particular relation necessary to permit percutaneous administration on the basis of the molecular planning of the polymer molecules. That is, the polyoxyalkylene constructing the hydrophilic part in Japanese Patent Publication No. 9922/86 cannot be merely simplified as a hydrophilic compound. In practice, from the viewpoint of a molecular structure, the degree of the hydrophilicity or hydrophobicity varies depending upon a ratio of the number of methylene group in the alkylene group and the ether-oxygen or a molecular weight. In case the proportion of the methylene group is high, it becomes practically water-insoluble hydrophobic or lipophilic compound Therefore, Japanese Patent Publication No. 9922/86 does not include an universal principle control release of drugs.

On the other hand, in accordance with the present invention, as described hereinafter, the polyoxyalkylenes are orderly arranged, and the molecular-planning of a hydro-philicity-hydrophobicity tapered polymer and the controlled release of a drug are carried out in consideration of the controlling of the interaction in molecular level between a drug and a polymer.

Recently, mixture systems of pharmaceutical substance/polymer have been extensively studied not only with respect to the pharmacological element but also from the standpoint of the technical field of polymer science. Under the circumstances, the development of polymers which are specifically usable for determined drugs and of the principle of the release of the drug component on the basis of the function of the specific polymers is of course necessary. Moreover, the development of a universal controlled release system, using polymers having a molecular structure that can be changed precisely and strictly in accordance with pharmaceutical substances is earnestly desired.

Most of the above-mentioned conventional base substances which have heretofore been widely used are found in systems that a pharmaceutical component is merely carried by an adhesive agent, and the release of the pharmaceutical component as blended and dispersed in the adhesive agent is extremely poor. In addition, when the adhesiveness of the adhesive component in the system becomes insufficient because of a sweat component or the like, even the pharmaceutical substance present near the surface of the adhesive component cannot adequately penetrate the skin, and therefore, the pharmaceutical effect is likely to be insufficient. Although oily gels or aqueous gels are somewhat better than agents of the above-mentioned type with respect to the release of pharmaceutical components, they reduce the stability of pharmaceutical components. In addition, these preparations have poor retention of shape, when they are in the form of a thin films, and are inadequate with respect to solubility and dispersibility of pharmaceutical substances.

The study which has heretofore been developed on drugs for percutaneous administration roughly classifies one process from the diffusion of a pharmaceutical component in the preparations to the release thereof to a stratum corneum tissue and another process to the distribution of the pharmaceutical component into the stratum corneum tissue and the diffusion of the component into the epidermis, dermis and sub-dermis tissue Drugs for percutaneous administration fail to meet the requirements of either process and cannot be put in practical use.

One condition for an ideal system of a percutaneous administration of a drug is, first of all, that the pharmaceutical component is dissolved and dispersed in a base component as uniformly as possible. However, an excessively high solubility, where the base component and the pharmaceutical component are relatively strongly bonded state and the pharmaceutical component has a low active coefficient is unfavorable, since the rate of release of the pharmaceutical component is undesirably lowered. It is rather desired that the affinity between the pharmaceutical component and the base component be relatively low and that the pharmaceutical component have a high active coefficient, in order to enhance its smooth release. However, an insufficient affinity between the pharmaceutical component and the base component must also be avoided, since the free movement of the pharmaceutical component in the base component during storage of the percutaneous preparations may concentrate the pharmaceutical component in the surface part of an adhesive or permit the pharmaceutical component to bleed out of the adhesive. If so, an expensive drug will be lost, and the release of the pharmaceutical component from the adhesive, immediately after its application to the skin cannot be controlled efficiently. Accordingly, it is desirable that the base component and the pharmaceutical component be in the form of a uniform molecular dispersion where the two components are strongly bonded together or in a similar form thereto during storage, and that the bonded state between the two may be relaxed when the adhesives are applied. When a drug can be uniformly dissolved in a base substance which has a low affinity therewith and had a minimum solubility, the degree of the release of the drug will be elevated, which is economical. Other systems are being investigated, in which a drug is not dissolved in a base substance but is uniformly dispersed therein. One is a matrix-type drug delivery system, which may be a micro-seal type or a microreservoir type. In the former type, a drug which is generally liquid is dispersed in a polymer matrix in the form of a mixture with a powdery material to form a dispersion of micro-spheres. In the latter type, a co-solvent mixture comprising a drug and a liquid material is dispersed in a polymer matrix in the form of a micro-reservoir. In an emulsion-type base component where liquid particles are dispersed in a liquid material, it is considered advantageous to incorporate a fat-soluble drug in the oil phase which is a continuous phase of the W/O-type base component. In another instance, a W/O/W-type composite emulsion has been investigated as an emulsion-type base component of high sealability In spite of various studies as mentioned above, it has not been possible to discover an effective means which can consistently ensure a drug-release of high efficiency, although some improvement of the efficiency of the drug-release has been attained to a limited extent.

Drugs, whether conventionally taken by injection or oral administration, or novel drugs, are required to be administered through a pertinently selected administration pathway in accordance with the property of the drugs themselves, their pharmaceutical effect and their therapeutic object. A percutaneous administration has been employed to attain a local effect in the past, but recently, increasing attention is being paid to the use of such preparations for general systemic application. The variety of drugs which may be used by percutaneous administration has increased, and accordingly, the development of universal base components which can be used for various kinds of drugs of a broad range as well as permitting their sustained release is eagerly sought.

SUMMARY OF THE INVENTION

Accordingly, one object of the invention is to provide an adhesive for percutaneous administration of biological agents.

A second object of the invention is an adhesive permitting more careful control of the amounts and rate of percutaneous administration than heretofore possible, with consequently greater safety.

A further object is to provide an adhesive for percutaneous administration that permits stable storage of highly unstable drugs.

Another object of the adhesive for percutaneous administration according to the present invention is the sustained and efficient supply of a biological agent through the skin.

Yet another object of the present invention is an adhesive capable of wide applicability in transdermal applications, that can be easily and precisely modified to permit controlled administration of drugs having widely differing physical and therapeutic properties.

After long study, it has now been discovered that these and other objects of the present invention may be attained by an amphiphilic polymeric compound having both heat-sensitivity and water-sensitivity as a base component in a drug-containing layer provides a novel mechanism permitting universal diffusion, release and distribution of drugs, which is quite different from that in any other conventional base components and thus have accomplished the present invention.

Accordingly, the present invention relates to adhesives for percutaneous administration comprising a layer containing a heat-sensitive and water-sensitive amphiphilic polymer and a biologically active agent.

BRIEF DESCRIPTION OF THE DRAWINGS

FIGS. 1 to 4 show preferred embodiments of adhesives of the present invention, where (1) is a surface coat layer, (2) is a pressure-sensitive adhesive layer, (3) is a drug-containing layer, (4) is a release-control layer, (5) is a liner, and (6) is a rigid base support.

FIG. 5 is a graph to show the blood pressure depression obtained by the application of a conventional PEG ointment or the adhesives of the present invention to rats.

DETAILED DESCRIPTION OF THE INVENTION

Drugs may generally classified as lipophilic (hydrophobic) or hydrophilic, and as solid or liquid at normal temperature. Regarding the pharmaceutical effect of drugs, the effective dose largely varies from the order of mg/dose to that of μg/dose. In addition, some drugs are not stable to heat, water or air.

The present invention provides adhesives which contain a polymer base component capable of being adapted widely to any desired drug and having superior release characteristics resulting from the use of the polymer base component.

In general, compounds that are soluble in both polar solvents and non-polar solvents are called amphiphilic substances, which reversibly aggregate in water to form a micelle but form a reverse micelle in an oil. In the same manner, a block copolymer composed of a series of blocks of different molecules comprising hydrophilic blocks and hydrophobic (liophilic) blocks, when dissolved in a liquid that is a solvent only for one class of the blocks, forms stable colloidal particles. Accordingly, block copolymers of this kind are referred to herein as amphiphilic polymers, and are capable of forming a micelle like low molecular weight surfactants.

The amphiphilic polymers for use in the present invention also includes polymers having both hydrophilic blocks and hydrophobic blocks in one molecule, as mentioned above, where each block gradually differs in the degree of the hydrophilicity or in that of the hydrophobicity (the degree of lipophilicity) and the blocks are connected to each other so as to provide a gradient of hydrophilicity (or hydrophobicity) from one end of the complete molecule to the other end thereof.

The term "heat-sensitivity" as used herein means that the polymer is a solid which has a crystalline state or a non-crystalline state, when stored at normal temperature, and which can sharply sensitive to heat at a determined temperature or higher to melt. For instance, such polymers include those which are solid in the form of flakes or pastes at normal temperature and which can melt at a skin surface temperature of from about 30° to 37° C. to have a viscosity of from about several hundred centi-poises to 10,000 centi-poises so as to become suitable for a solid drug to be dissolved or dispersed and floated in the resulting viscous polymers. The amphiphilic polymers have, after having been converted into a liquid form at the relatively mild temperature of from about 30° to 37° C., a large solubilizing power and therefore can dissolve many kinds of drugs including both liquid and solid compounds because of the function of the constitutional blocks which are either hydrophilic or hydrophobic in the polymer. Accordingly, these polymer compounds can advantageously be used to uniformly blend a predetermined amount of a drug with a polymer base component in the preparation of the adhesives.

The term "water-sensitivity" as used to herein means that the amphiphilic polymers are hydrated in the region of the hydrophilic blocks therein, when brought into contact with water. In particular, polymers which are in the liquid phase because of the heat-sensitivity thereof have a more sharply-defined sensitivity to water. For instance, water-sensitivity varies as follows, depending upon the characteristics of polymers.

(A) In the case of polymers which have a relatively small total molecular weight and a low melt viscosity:
  (1) Polymers where the complete molecule is predominantly hydrophobic are naturally emulsified in the interface between the polymer and water to form microspheres in the form of grains having a grain size of about 0.1 to 100 μ or so, whereby the polymer naturally moves into the aqueous phase.
  (2) Polymers where the complete molecule is predominantly hydrophilic are emulsified when brought into contact with water, and thereafter immediately dissolved in the water. Alternatively, the polymer is dissolved from the surface thereof which is kept in contact with water.

(B) In the case of polymers which have a relatively large total molecular weight and a high melt viscosity:
  (1) Polymers where the complete molecule is predominantly hydrophobic are brought into contact with water, the polymer is hydrated in the position of the hydrophilic blocks as existing in the interface between the water and the polymer, at a slow rate. The whole of the base polymer is hydrated in a relatively long period of time, but the polymer hydrated is not completely emulsified, but remains a viscous liquid However, as the apparent melting temperature of the polymer decreases, after hydration, the polymer hydrated becomes more heat-sensitive. Polymers of this type are advantageously used as a base component for lipophilic drugs, which are to be directly released and distributed into the skin without using any control film.

(2) Polymers where the complete molecule is predominantly hydrophilic are brought into contact with water, the hydrophilic segment in the polymer is immediately hydrated, and the hydration proceeds further until the polymer is completely dissolved. Accordingly, the apparent melting point of the polymer hydrated decreases and the hydration of the polymer proceeds in the antagonistic molten and dissolved states. The polymer thus hydrated will gradually move to the surface of the skin and spread thereover, although it has no flowability as the above case (A)-(2).

In either event, after becoming liquid by application of heat or after dissolving by contact as sensitized with water, the polymer is a viscous liquid of appreciable to fairly high fluidity, and a drug is solubilized in the viscous liquid polymer in the form of a more uniform molecular dispersion than in the initial stage when the drug is first blended into the polymer. After solubilization, the drug molecule is released from the weak interaction with the polymer segment of high affinity on the contact surface of the skin and then is gradually distributed and absorbed into the inside of the skin.

Of the amphiphilic polymers for use in the present invention, the proportion of hydrophobic and hydrophilic components and the molecular weight are selected to make the polymer compounds water-sensitive and heat-sensitive as defined above. After the polymer melts or dissolves, the hydrophilic blocks in the polymer compound solubilize a hydrophilic low molecular compound and the hydrophobic blocks therein have an action to solubilize a hydrophobic low molecular compound In general, drugs also can be classified into those which are soluble in a polar solvent and others which are soluble in a non-polar solvent. Alternatively, these can further be roughly classified into hydrophilic drugs and hydrophobic drugs Accordingly, the polymer compounds of the present invention which are composed of different blocks each having a gradually varying degree of hydrophilicity or hydrophobicity (lipophilicity) may advantageously be selected for dissolving the various corresponding drugs. The polymers of the present invention can solubilize any drug, whether lipophilic or hydrophilic, liquid or solid. An outstanding advantage of the preparation according to the present invention is that even a slight amount of a physiologically highly active substance which is solid and is easily decomposed, and which has heretofore been considered quite difficult to be solubilized, can be solubilized in the polymers of the present invention to form an adhesive for percutaneous administration. The present invention is extremely meaningful in this respect.

As the base component for use in the present invention, any and every amphiphilic polymer can be utilized, provided that they are heat-sensitive and water-sensitive Preferably, the heat-sensitive and water-sensitive amphiphilic polymers for use in the present invention are block polymers having a higher degree of hydrophilicity at one end of the polymer molecule and a higher degree of hydrophobicity or lipophilicity at the other end of the polymer molecule, and in particular, the polymers of the present invention preferably have a melting point falling within the range of from about 30° to 37° C. in order that the drugs in the adhesives can stably be preserved while stored and that the polymers can melt nearly at skin surface temperature to release the drug component therefrom when applied to the skin. More preferably, the amphiphilic polymers are a multi-block copolymer comprising a reaction product of an alkyleneoxide-polyether-polyol, an aliphatic polyesterpolyol or an aliphatic polyether-polyol and a diisocyanate, and such polymers may be represented by the following general formula (A):

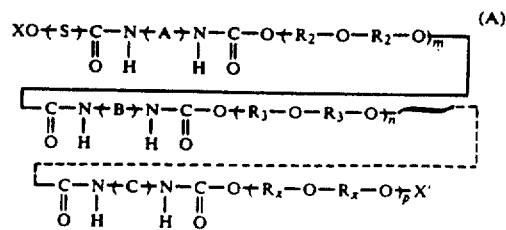

wherein (S) is selected from the group consisting of (a) a polyalkylene segment represented by the following general formula (I):

wherein $R_1$ to $R_x$ each represents an alkylene group having from 7 to 2 carbons, the number of carbon atoms in each group of the series $R_1$ to $R_x$ being less than the number of carbon atoms in the previous alkylene groups of the series from $R_1$ to $R_x$, provided that the number of carbon atoms in any two immediately adjacent members of the series $R_1$ to $R_x$ may be equal, and any alkyleneoxide group containing the alkylene group of the series from $R_1$ to $R_x$ may be omitted;

(b) an aliphatic polyester segment which is the reaction product of a dibasic acid and a dihydric alcohol represented by the following general formula (II):

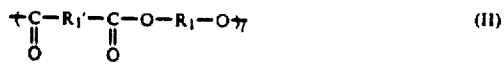

wherein $R_1$ and $R_1'$, which may be the same or different, each represents an alkylene group, R represents an alkylene group of dihydric alcohol, the total number of carbon atoms in $R_1$ and $R_1'$ is greater than the number of carbon atoms in $R_2$, $R_2$ to $R_x$ each represents an alkylene group having from 4 to 2 carbon atoms, the number of carbon atoms in each group of the series $R_2$ to $R_x$ being less than the number of carbon atoms in the previous alkylene groups of the series from $R_2$ to $R_x$, provided that the number of carbon atoms in any two immediately adjacent members of the series $R_2$ to $R_x$ may be equal, and any alkyleneoxide group containing the alkylene group of the series from $R_2$ to $R_x$ may be omitted; and (c) a polyester segment which is the reaction product of a ring-cleaved polymer of a cyclic ester and a dihydric alcohol represented by the following general formula (III):

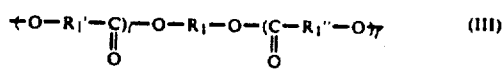

melting point and may mostly be liquid, and therefore, these are suitably used as the segments in the polymers of the present invention. In this connection, the polymer segments may be readily selected by one skilled in the art under consideration of the characteristics of the finished complete polymers including the hydrophilicity-hydrophobicity balance, melting point, viscosity and affinity with drugs. Specific examples of polyesters which have a melting point of about 30° to 37° C. or so, or which are liquid include polyester-polyols obtained from the following combinations:

Ethylene glycol and glutaric acid, pimelic acid or azelaic acid;
Propylene glycol and succinic acid, glutaric acid, adipic acid, pimelic acid, suberic acid, azelaic acid or sebacic acid;
Butane-diol and glutaric acid or pimelic acid;
Hexane-diol and succinic acid, glutaric acid, adipic acid, pimelic acid or suberic acid;
Eicosane-diol and azelaic acid;
Diethylene glycol and suberic acid or sebacic acid;
Triethylene glycol and sebacic acid;
Neopentyl glycol and succinic acid, adipic acid, suberic acid, azelaic acid or sebacic acid, etc.

In addition, poly-3-methyl-pentane-1,5-diol adipates are also liquid, having a low viscosity; and those having a molecular weight of from 1,000 to 3,000, among them, can be used in the present invention.

Of suitable polyesters comprising the combination of a glycol and a dicarboxylic acid, those having a low molecular weight (within the range of about 500 to 3,000, preferably about 500 to 1,000 are selected for use in the present invention. The polyester segments are necessarily more hydrophobic than the adjacent polytetramethylene glycol segments, and therefore, the polyesters having 5 or more methylene groups are advantageously used in the present invention. The difference between the ester bond of the polyester segment and the ether bond of the polyether segment is considered to influence the relation of the hydro-philicity-hydrophobicity in the block copolymers, which is one problem. In this connection, the present inventors' experiments have confirmed that the ester bond has a strong intermolecular cohesive force in the solid state and that the polyesters have a stronger affinity than the polyethers to solvents which are more lipophilic. Accordingly, the block copolymers, even though having a low molecular weight, are hard and waxy in the solid state because of the intermolecular forces of the ester bond; but they can be converted into a liquid having a low viscosity, when melted. For this reason, it is easy to obtain block copolymers having a definite melting point and a clear viscosity variation. These characteristics of the block copolymers obtained differ from those of other amphiphilic segment polyurethanes containing only polyalkyleneoxides having from 5 to 7 carbon atoms as the lipophilic segments, and the block copolymers of the present invention are harder in the solid state, have a more definite apparent melting point and have a lower viscosity when melted, than such amphiphilic segment polyurethane. In the preparation of the block copolymers according to the present invention, the polyesters can be selected from many polyesters in a broad range, including liquid polyesters, to obtain many kinds of block copolymers of a broad range, having a variety of hydrophobicity-hydrophilicity balances. This is one characteristic feature of the present invention.

In addition, ring-cleaved polymers of a cyclic ester having 5 carbon atoms can also be used for the same object. For instance, one example comprises a ring-cleaved polymer of ε-caprolactone and a polyester glycol such as diethylene glycol. The ring-cleaved polymers are preferably selected to have a molecular weight of from about 500 to 2,000, more preferably from about 500 to 1,000. Further, poly-βmethyl-δ-valerolactone-glycols can be used as a liquid polyester having a low viscosity, provided that these have a molecular weight of from about 1,000 to 3,000.

The polyether-glycols suitable for forming the polyalkyleneoxide segments in the block copolymers of the present invention are now described in greater detail. Polyalkyleneoxides are generally synthesized by ring-cleaving polymerization of a cyclic ether compound. Such polymers have a higher hydrophilicity with the decrease of the number of the methylene groups in the alkyleneoxide, since the proportion of the ether-oxygen in the polymer is larger; and conversely, these have a higher hydrophobicity with the increase of the number of the methylene groups in the alkyleneoxide, since the proportion of the ether-oxygen in the polymer is smaller. The alkyleneoxides having more methylene groups are considered hydrophobic, because the association between the ether-oxygen in the alkyleneoxide and water is inhibited by the structural hindrance of the methylene group chain, although the ether-oxygen has an affinity with water. In other words, the alkyleneoxides become more hydrophobic with the increase of the number of methylene groups, for the following reasons.

When brought into contact with water, the alkyleneoxide will act to repel the water since there is less affinity between the methylene group and water, and the alkyleneoxide is most stable in non-hydrating surroundings. This self-associating phenomenon is called a "hydrophobic interaction". In order to decrease the hydrophobic contact with water, the molecular volume increases due to self-association, and the number of CH units has a great influence on the increase of the volume. That is, alkyleneoxides having a large number of $CH_2$ units are said to be more hydrophobic. The proportions of the oxygen and carbon in polyhexamethylene glycol, polytetramethylene glycol, polypropylene glycol and polyethylene glycol is 1/6, ⅕, ¼, and ⅓, respectively. In addition, in the case of polyalkyleneoxides, a polymeric effect is added to the hydrophobic effect of the monomer unit. Accordingly, polyalkyleneoxide segments having 5 or more carbon atoms are more lipophilic than hydrophobic.

In the present invention, alkyleneoxide polymers are used having a low polymerization degree, to form segments in the amphiphilic block copolymers, and may readily be selected by one skilled in the art by considering the characteristics of the resulting block copolymers, including the hydrophilicity-hydrophobicity balance, melting point, viscosity, affinity with drugs, etc. In general, the molecular weight of the alkyleneoxide polymers for use as segments in the present invention is roughly limited to the range of about 500 to 3,000, preferably about 500 to 1,000.

The lipophilic polyalkylene glycols for use in the present invention are not limited, and may any known compounds obtained by ring-cleaving polymerization, which include, for example, polypentamethylene glycols, polyhexamethylene glycols, polypeptamethylene glycols, etc. In general, block copolymers having these wherein $R_1'$ and $R_1''$, which may be the same or different, each represents a reaction of a ring-cleaved polymer of a cyclic ester containing 5 carbon atoms, $R_1$ represents an alkylene group of the dihydric alcohol, $R_2$ to $R_x$ each represents an alkylene group having from 4 to 2 carbon atoms, the number of carbon atoms in each group of the series $R_2$ to $R_x$ being less than the number of carbon atoms in the previous alkylene groups of the series from $R_2$ to $R_x$, provided that the number of carbon atoms in any two immediately adjacent members of the series $R_2$ to $R_x$ may be equal, and any alkyleneoxide group containing the alkylene group of the series from $R_2$ to $R_x$ may be omitted; and in general formula (A), —OX represents a group selected from the group consisting of RO—, RCOO—,

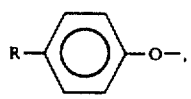

R—NHCOO—, and ROOCHN—Ⓟ—NHCOO—, wherein R represents an alkyl group having 1 to 18 carbon atoms or a vinyl group and Ⓟ represents an isocyanate skeleton group; —OX' represents a group selected from the group consisting of —OH, —OCl, —OBr and —OF; l, l', m, n and p, which may be the same or different, each is a positive integer; and (A), (B) and (C), which may be the same or different, each represents an isocyanate skeleton group.

In the polymers of the general formula, the polyester segments are lipophilic, the polyalkyleneoxide segments having 5 or more carbon atoms are lipophilic, the polyalkyleneoxide segments having 4 or 3 carbon atoms are hydrophobic and the polyalkyleneoxide segments having 3 or 2 carbon atoms are hydrophilic. The hydrophilicity (or hydrophobicity) of polypropylene glycol segments having 3 carbon atoms largely depends upon their molecular weight. The amphiphilic polymers of the present invention are selected such that the degree of the hydrophobicity (or the degree of the hydrophilicity) exhibits a gradient from one end of the molecule to the other end thereof; such a polymer is referred to herein as a hydrophobicity-hydrophilicity tapered block polymer. Specifically, the polymers are composed either of (a) a polyester segment (comprising a dibasic acid and a dihydric alcohol or a ring-cleaved polymer of a cyclic ester), or a polyalkyleneoxide segment comprising an alkyleneoxide having from 5 to 7 carbon atoms; (b) a polytetramethylene glycol segment; (c) a polypropylene glycol segment; and (d) a polyethylene glycol segment, from the hydrophobic side to the hydrophilic side in order. These segments are connected to each other by a diisocyanate. Of the polymers of this kind, multi-block polymers of from binary to hexanary are preferred, comprising different kinds of segments having the hydrophilicity-hydrophobicity tapered gradient sequence. Alternatively, the polymers may be multi-block copolymers as composed of a polymer comprising a combination of segments of the same kind with which other different kinds of segments are connected, and/or the polymers may be others where the segments are partly omitted without being continuously connected with each other.

The hydrophilicity-hydrophobicity tapered amphiphilic segment polyurethanes which are both heat-sensitive and water-sensitive, for use in the present invention, are explained in greater detail hereinafter.

The polymers for use in the present invention preferably have a melting point within the range of about 30° to 37° C., so that the drug as incorporated in the adhesives may be stably preserved while the adhesive is stored and that the polymer will melt at skin surface temperature to release the pharmaceutical component from the adhesive when the adhesive is actually applied to the skin. The apparent melting point of the segment polymer depends upon the melting point of each constitutional segment. Each segment polymer for constituting the polymers of the present invention may either be liquid or solid at normal temperature as a polyester glycol or polyether glycol. However, if liquid polymers only or solid polymers having a melting point of 37° C. or higher only are connected as segments, it is impossible to obtain segment polyurethanes which melt at a temperature of from 30° to 37° C. The combination of polymers which melts at 30° to 37° C. is preferred, but liquid polymers and solid polymers may be connected. The use of liquid polymers as segments is extremely interesting from the viewpoint of the release of a pharmaceutical component therefrom, since the interaction between the liquid polymer and the pharmaceutical component differs from that of a solid polymer because of the thermal movement of the liquid polymer. In case liquid segments are incorporated into the block copolymer, a solid polymer having a fairly high melting point can be connected therewith, depending upon the ratio of the segments between the liquid polymer and the solid polymer. Polymers having a melting point of up to about 50° C. can be used as segments, because the apparent melting point of the resulting block polymer will decrease due to the molecular movement of the liquid segment or the melting point thereof will decrease due to the sensitization with water. However, it is generally preferred to connect solid polymers having a melting point of about 30° to 37° C. and liquid polymers by a diisocyanate component. In addition, the block copolymers are required to melt to become a liquid having a low viscosity, and therefore, the polymers forming the respective segments should be compounds having a relatively low polymerization degree.

The polyester glycols as a lipophilic segment are now described in greater detail The polyester glycols which can be used in the present invention are preferably aliphatic polyesters, since these are required to have a low melting point and a low melt viscosity, as mentioned above, and the total number of carbon atoms in the methylene groups of $R_1$ and $R_1'$ is greater than number of carbon atoms in $R_2$ and less than 30. There are many suitable aliphatic polyesters, known in the art as comprising a combination of an aliphatic dicarboxylic acid and a glycol. In general, aliphatic polyesters having a low molecular weight are brittle and waxy, and those having a high molecular weight are tough and keratinous. Accordingly, waxy aliphatic polyesters having a low molecular weight are preferably used in the present invention. The melting point increases with the increase of the molecular weight in these polyesters, but those having a relatively low molecular weight have an almost constant melting point. Each polyester comprising a combination of a dicarboxylic acid and a dihydric alcohol has an intrinsic melting point. The polyesters for use in the present invention are roughly restricted to having a molecular weight of about 500 to 3,000 or so. In general, polyesters having side chains as introduced thereinto so as to enlarge the intermolecular length and to lower the molecular symmetricity will have a low polyalkylene oxide as the lipophilic segment have a higher melt viscosity than those having polyester segments Accordingly, polyalkylene oxide block copolymers are suitable for use in adhesives for percutaneous administration where the copolymer acts as an adhesive in the form of a tacky state containing a drug dissolved therein and is directly applied to a skin without using any control film.

Hydrophobic or hydrophilic alkyleneoxide polymers suitable for use in the present invention are now described in greater detail. Polytetramethylene glycols are hydrophobic segments, which are insoluble in water but are highly soluble in ethanol. Of polytetramethylene glycols, those having a molecular weight of from about 500 to 3,000 can be used in the present invention, as these have a proper melting point. Specifically, those having a molecular weight of 650, 1,000, 2,000 or 3,000 have a melting point of 11° to 19° C., 25 to 33° C., 28° to 40° C. or 30° to 43° C., respectively. Polypropylene glycols remain liquid, even though having a molecular weight of 40,000 or so, and these can be utilized as a liquid segment. Of polypropylene glycols, those having a molecular weight of 750 or less are soluble in water, while those having a molecular weight of higher than 750 are scarcely soluble or insoluble in water. Accordingly, suitable polypropylene glycols may readily be selected by one skilled in the art by considering the desired characteristics of the resulting block copolymers, including the hydro-philicity-hydrophobicity balance, melting point depression effect affected by the liquid segment-solid segment balance, melt viscosity, etc. Polypropylene glycols have a noticeable molecular weight effect to the hydrophobicity, as having CH$_3$ group in the side chain, requiring attention to be paid to the interaction between the propylene glycols and drugs.

Polyethylene glycols form water-soluble segments. Of polyethylene glycols, those having a molecular weight of about 600 or less are liquid at normal temperature. As a solid segment, those having a molecular weight of from about 800 to 1,000 (and having a melting point of from about 30° to 38° C.) can be used, although polyethylene glycols having a molecular weight of up to about 2,000 (and having a melting point of up to 48° C.) can be used, provided that these are well balanced with other liquid segments. With polyethylene glycols, hydrophobicity increases with molecular weight, because of the polymeric effect thereof. Polyethylene glycols are polymers having a high crystallinity, and in the liquid phase have an extremely low melt viscosity especially in the state containing water. In addition, these have a sharp melting point. Accordingly, the polyethylene glycols are the most important factor determining the melting point and the melt viscosity of the amphiphilic polyurethanes for use in the present invention. In addition, polyethylene glycols repel non-polar substances, and therefore have a great influence on the mechanism of releasing a non-polar drug from the amphiphilic polymer. Further, the ether-oxygen in the alkyleneoxide in these polyethylene glycols have a weak interactivity with drugs, and therefore, the polyethylene glycols are almost free from the danger of decomposing a drug by reaction.

The respective segments may advantageously be connected with each other by a diisocyanate in such sequence that the carbon number of the monomer unit in each segment is to be 2, 3, 4, 5, ... x in order, in order to obtain the desired hydrophilicity-hydrophobicity tapered amphiphilic segment polyurethanes In the polyurethanes obtained, heat-sensitivity and water-sensitivity depend upon the kind and molecular weight of each constitutional segment, the molecular weight balance or the total molecular weight of the resulting polyurethane. If desired, the polyurethanes need not be always constructed by all the segments in a series, according to the object thereof, but the segments may partly be omitted. Alternatively, two or more segments of the same kind may be connected by a diisocyanate, if the required hydrophilicity-hydrophobicity balance, melting point and melt viscosity are met by the resulting polyurethanes. In particular, the connection of two or more polyethylene glycols is advantageous in order to intensify hydrophilicity and maintain a definite melting point of from 30° to 37° C.

For this reason, the connection of two or more polyester-glycols can be taken into consideration. However, the duplication of same segments by connecting the same polyester-glycol segments with a diisocyanate is not preferred because the hydrophobic effect is remarkable, the melt viscosity increases with the increase in the number of urethane bonds, the melt viscosity increases with the increase in the molecular weight, and the increased number of the polymerization reactions is troublesome and complicated.

The total molecular weight of the thus-connected amphiphilic segment block copolymers is selected to fall within a range of about 1,500 to 10,000, preferably about 2,000 to 5,000 in consideration of the melt viscosity thereof.

The —OH group in the hydrophobic segment end is deactivated with any known alkyl group imparting hydrophobicity, in a conventional manner. If, however, the alkyl group used therefor is too large, the melting point of the segment is increased, resulting in the elevation of the melting point of the complete polymer. Accordingly, the alkyl group preferably is one having from 1 to 18 carbon atoms. For instance, when the end group is a monoisocyanate represented by a formula RNCOO—, CH$_3$(CH$_2$)$_{17}$NCO is an effective hydrophobic end-deactivating agent, having a melting point of 19° C. On the other hand, the end in the hydrophilic side can easily be synthesized, and —OH group which is non-toxic is most useful.

As the isocyanate compounds for connecting the segments of the polynary block copolymers of the present invention, various diisocyanates may be used, including, for example, p-phenylene-diisocyanate, 2, 4-toluylene-diisocyanate (TDI), 4, 4'-diphenylmethane-diisocyanate (MDI), naphthalene-1, 5-diisocyanate, hexamethylene-diisocyanate, lysine-diisocyanate, xylene-diisocyanate, hydrated TDI, hydrated MDI, dicyclohexyldimethylmethane-p, p'-diisocyanate, diethylfumarate-diisocyanate, isophorone-diisocyanate, etc. These isocyanates may suitably be used as the groups represented by (A), (B), (C) and ⓓ in the above-mentioned formula, and these may be same or different. After the segments have been connected with the isocyanate compounds, the resulting polymer is preferred to have a conformation capable of facilitating the interaction between the methylene group or the ether-oxygen (a part of which is a carbonyl group of a polyester) and a pharmaceutical component. Accordingly, the diisocyanate component is preferably so positioned that the isocyanate is in a linear form rather than in an angled form, whereby linear-connected polymers can easily be formed. In particular, polymers comprising aliphatic segments and aliphatic diisocyanates are preferred, as these are relatively brittle, waxy and solid in a molecular range which is suitable for use in the present invention, and further these have a definite melting point and a low melt viscosity. Specifically, tetramethylene-diisocyanate, hexamethylene-diisocyanate, etc. are preferably used.

As mentioned above, molecular planning of the polymers for use in the present invention is determined by the controlled hydrophilicity-hydrophobicity (lipophilicity) tapered structure and the heat-sensitive and water-sensitive function. As an auxiliary agent for assisting the heat-sensitivity and water-sensitivity of the amphiphilic segment polyurethanes of the present invention, polyethylene glycols, propylene glycols or copolymers of these two or similar series surfactants, which have a molecular weight capable of meeting the condition of the present invention, can optionally be added to the polyurethanes, if desired.

Examples of preferred combinations of segments for use in the present invention are given in the following Table 1. However, the combinations of segments for use in the present invention are not whatsoever limited to those as illustrated in the examples, which are provided only for purposes of illustrating specific embodiments of the present invention. Following Table 1, a general flow-sheet of the synthesis of the polymers of the present invention is set forth.

The amphiphilic polymer of the present invention can be synthesized in accordance with the process as described, for example, in Japanese Patent Application No. 111477/86 filed on May 14, 1986.

TABLE 1

| | Example No. | | | | | | | |
|---|---|---|---|---|---|---|---|---|
| | 1 | 2 | 3 | 4 | 5 | 6 | 7 | 8 |
| Segment (Mw) | | | | | | | | |
| PAO (I) | 500*1 | 1,000*1 | | | | | | |
| PES (II) | | | | | | | 1,000*3 | 800*4 |
| PES (III) | | | | | | 530*2 | | |
| PTMG | 2,000 | | 2,000 | 1,000 | 650 | | | 650 |
| PPG | 1,000 | 1,000 | 2,000 | 1,000 | 400 | 400 | 400 | 400 |
| PEG | 800 | 1,000 | 1,000 × 3*5 | 1,000 | 1,000 | 1,000 | 1,000 | 1,000 |
| Total Mw | 4,900 | 3,400 | 7,500 | 3,400 | 2,450 | 2,330 | 2,800 | 3,400 |

Notes:
PAO: Polyalkyleneoxide
PES: Polyester
PTMG: Polytetramethylene glycol
PPG: Polypropylene glycol
PEG: Polyethylene glycol
*1 Polyhexamethylene glycol
*2 Poly-ε-caprolactone
*3 Poly-3-methyl-pentane-1,5-diol-adipate
*4 Polybutylene-adipate
*5 Three PEG-1000's were connected together.
The isocyanate was hexamethylene-diisocyanate.
The hydrophobic end was deactivated with butyl isocyanate; and the hydrophilic end was —OH.

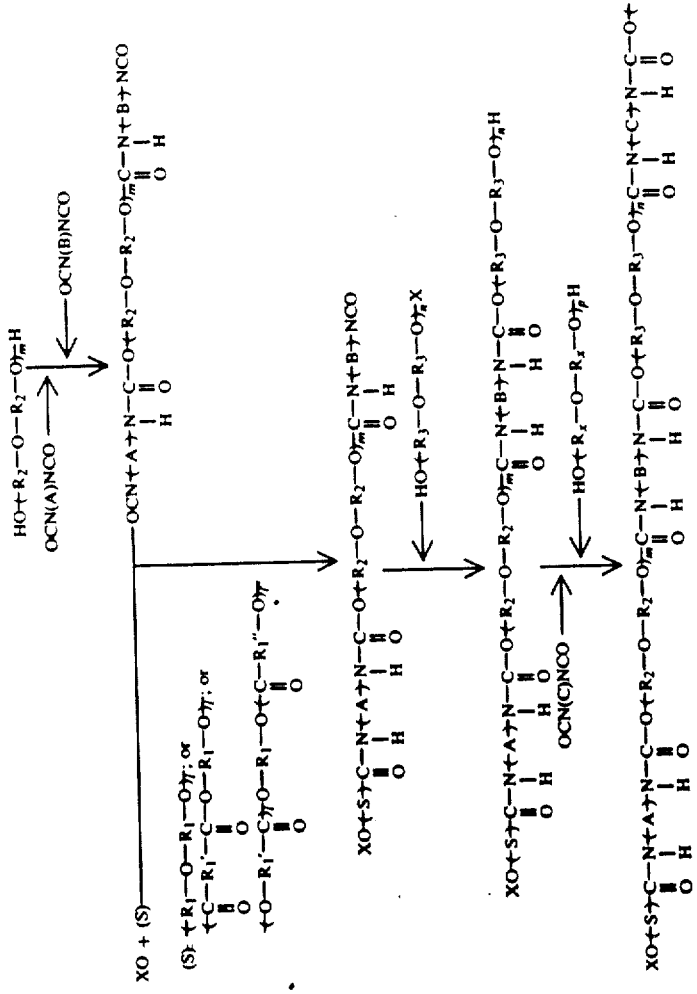

Then, the mixture of the polymer synthesized and a drug is carried out, by any conventional method well-known in the art, typically as follows: In the first place, a solid polymer is weighed at a temperature lower than the melting point of the polymer. A suitable quantity of a desired drug is measured by volume or by weight and heated at 30° to 37° C. to give a viscous liquid. This is added to the polymer and the mixture is well kneaded, in a vacuum or in an inert gas such as N or the like and in a dry state, which is more safe. The kneading temperature may be somewhat higher than the melting point of the polymer, and an extremely mild condition can be selected. The resulting mixture may be applied on the surface of a support to produce an adhesive.

According to this method, a solvent or auxiliary agent for blending is unnecessary, and therefore, a complicated treatment for removing the solvent later is unnecessary and attention to the safety of a residual solvent is also unnecessary. The polymer, as comprising a hydrophobic part and a hydrophobic part, has a function as a polymer surfactant, when liquid, and therefore, its solubilizing power is great, as is demonstrated by the fact that even a cyclo-dextrin-clathrate drug can gradually be dissolved by the polymer. Accordingly, the polymer can dissolve a variety of drugs of a broad range. A solid drug can be dissolved in the polymer, while the polymer is liquid at a low temperature, and therefore, the polymer provides the significant advantage of stability in treating such drugs. After being blended (or dissolved) in the polymer, the drug is maintained in the polymer in the form of a solid. For this reason, the preservation-stability of the drug is good; the drug does not bleed out of the polymer while stored, and the content of the drug does not vary.

In general, it is considered that the degree of toxicity, mucous membrane stimulation, skin primary-stimulation, etc. of surfactants varies, generally in the relationship cationic > anionic > ampholytic > non-ionic surfactants. The polymers of the present invention, which are non-ionic, are therefore highly safe. Further, the safety of the present polymers is supported be the fact that polyurethane resins comprising alkyleneoxide segments are considered usable as materials of artificial organs. In addition, we actually confirmed that the present polymers are not almost irritation in use.

The effect resulting from the hydrophilicity-hydrophobicity tapered structure of the polymers of the present invention is considered to be as follows, although the present invention is not limited in any way by the theoretical explanation or mechanism of its effectiveness.

The drug as blended with the polymer is mostly found near the segments having the highest affinity with the drug, and is dissolved therein in the form of a molecular dispersion. that is, a hydrophilic (or hydrophobic) drug generally is associated with the corresponding hydrophilic (or hydrophobic) segments in the polymer and is practically absent in hydrophobic (or hydrophilic) segments therein, and it is assumed that the drug will be dissolved in the polymer in a concentration corresponding to the molecular level concentration gradient. After the polymer is melted or dissolved in use and the drug is gradually absorbed through the surface of a skin, the concentration of the dispersion of the drug molecules will vary accordingly. However, the remaining drug molecules will thereafter move to the part of the polymer having a higher affinity with the drug and thus the pharmaceutical components will then be released from one molecular end of the polymer, the tapered gradient in the polymer participating in controlling the smooth movement and release of the pharmaceutical component. The polymers comprising segments connected to form a tapered structure provide a "field" where the direction of the release of any of hydrophilic drugs or hydrophobic drugs is continuously controlled.

The drugs that can be incorporated in the drug-containing layer of the adhesive of the present invention are not limited in any way, provided that they are used for percutaneous administration. The drugs may be hydrophilic or lipophilic, or may be either liquid or solid, and any such conventionally known drug can be used advantageously in the present invention. For instance, examples of the compounds which can be used in the present invention are set forth below, although the list provided is merely illustrative and does to limit the scope of the present invention.

(a) Prostaglandins (PG's) (e.g., PGA, PGD, PGE, PGF, PGI 6-keto-PGE, 6, 9-nitrilo-PGI, 6, 9-methano-PGI$_2$ and derivatives thereof, etc.)
(b) Vasodilatives (e.g., nitroglycerin, etc.)
(c) Corticosteroids (e.g., hydrocortisone, betamethasone, etc.)
(d) Anti-inflammatory agents (e.g, indomethacin, ibuprofen, etc.)
(e) Antibiotics (.g., penicillin, erythromycin, etc.)
(f) Hypnotic sedatives (e.g., phenobarbital, etc.)
(g) Anesthetics (e.g., benzocaine, etc.)
(h) Antibacterial agents (e.g., pentamycin, etc.)
(i) Vitamines (e.g., vitamin A, etc.)
(j) Anticonvulsants (e.g., atropine, etc.)

The content of the drug to the base component is properly determined in accordance with various factors including the strength of the drug, the age and condition of a patient, the desired therapeutic effect, the place to which the adhesive is to be applied and the intended period for the release of the drug.

The adhesives of the present invention include the essential constitutional elements of a drug-containing layer which comprises a heat-sensitive and water-sensitive amphiphilic polymer and a drug, which can optionally be used in combination any other layers in consideration of various factors including the simple usability of the adhesive, the stability, each releasability or slow releasability of the drug contained and the adhesiveness of the adhesive to a skin. Such additional layers include, for example, a surface coat layer, a pressure-sensitive adhesive layer, a rigid base support, a release-controlling layer, a liner, etc. These layers can be used in the adhesives of the present invention, for example, as shown in the drawings attached hereto. While the drawings illustrate certain embodiments of the adhesives of the present invention, concretely explaining the characteristics of the present invention and the mechanism of diffusion and release of a drug from the adhesives, they are not intended to restrict the scope of the present invention in any way. The actions of various kinds of layers, rigid base supports and liners will be evident from consideration of the drawings.

Figure 1B:
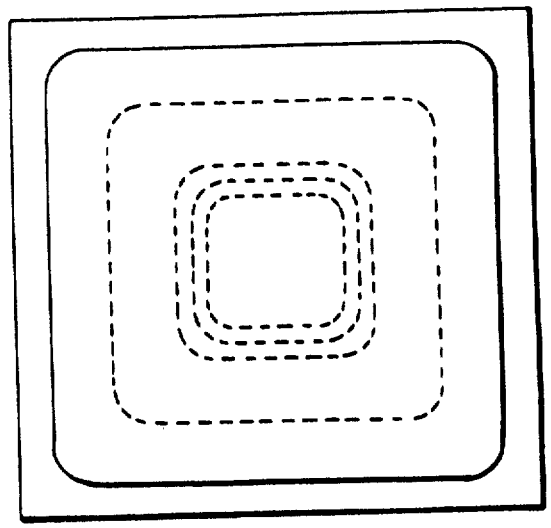
Figure 2A:
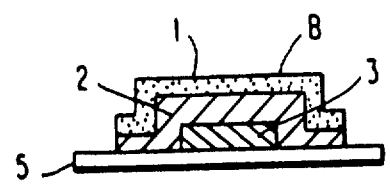
Figure 2B:
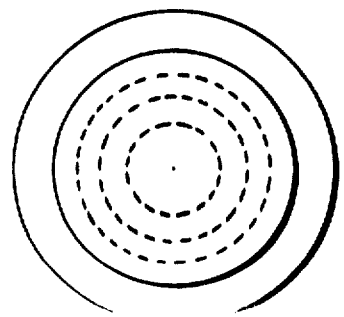

FIG. 1 shows a sectional view and a plane view of an adhesive (A) of the present invention, which is composed of a surface coat layer (1), a pressure-sensitive adhesive layer (2), a release-controlling layer (4) and a liner (5) in addition to a drug-containing layer (3). FIG. 2 shows a sectional view and a plane view of an adhesive (B) of the present invention, which is composed of a surface coat layer (1), a pressure-sensitive adhesive layer (2) and a liner (5) in addition to a drug-containing layer (3). FIG. 3 shows a sectional view of an adhesive (C), where a rigid base support (6) is added to the adhesive (A) of FIG. 1. FIG. 4 shows a sectional view of an adhesive (D), where a rigid base support (6) is added to the adhesive (B) of FIG. 2.

In such embodiments, the surface coat layer (1) functions not only as a support for the adhesive but also to prevent the drug from bleeding out to the side opposite to the side of a skin and to prevent the adhesive from being moistened during storage. The pressure-sensitive adhesive layer (2) has the function of adhering the drug-containing layer (3) to the surface coat layer and to adhere the whole of the adhesive to the skin under pressure. In addition, it prevents the drug from bleeding out to the side of the surface coat layer. The release-controlling layer (4) controls the release of the drug as well as reducing skin irritation and controlling the rate of release and the durability of the drug. When the base polymer component has a sufficient matrix-controlling function due to its interaction with a drug, the release-controlling layer (4) is unnecessary. The liner (5) prevents the adhesive from being moistened during storage, and is peeled off just before use of the adhesive. The rigid base support (6) presses the drug-containing layer (3) and the release-controlling layer (4) against the skin to intensify the adhesiveness of the adhesive to a skin and to prevent the adhesive from detaching from a skin. In addition, this may prevent the drug from migrating to the side of the surface coat layer (1).

Each of these layers is well-known in the art, and may typically be composed of the following materials.

In general, a synthetic resin film is used as the surface coat layer (1), including, for example, polyethylenes, polypropylenes, soft polyvinyl chlorides, ethylenevinyl acetate copolymers, ethylene-vinyl alcohol copolymers, polyethylene terephthalates, etc. The sensation of physical disorder in skin to which an adhesive has been applied is considered to be one cause of an eruption on the skin by the adhesive. That is, the sensation of an adhesive against skin occurs not only during application but afterwards as well, because of the tension of the skin during contact. If a low modulus material is used for the surface coat layer, having good flexibility and stretchability and sufficient softness and feeling, the compatibility of the adhesive with the skin will be good and the feeling of physical discomfort on the skin during contact will be less noticeable. Materials which can meet this condition are those having 100% modulus of about 5 kg/cm$^2$ or less, including, for example, soft polyurethane films, soft polyvinyl chloride foams, ethylene-vinyl acetate foams, 1, 2-polybutadiene foams, etc. Among them, 1, 2-polybutadiene foams are most preferred, as they are not blocked, may be made thin, and do not permit additives such as a plasticizer, etc. to bleed out and are highly safe. The thickness of the surface coat layer is preferably from about 0.15 to 1.0 mm, in consideration of the easiness for handling. The material of the surface coat layer may optionally be provided with a surface treatment agent on the inside or outside thereof for the purpose of preventing a drug from bleeding out from a base component. (When the surface treatment agent is provided on the outside of the surface coat layer, the agent further reduces friction when an adhesive is being worn.) The low modulus surface coat material forms an integrated structure together with the inner pressure-sensitive adhesive, as being fit for the modulus of the pressure-sensitive adhesive.

The pressure-sensitive adhesive (2) can be selected to be lipophilic or hydrophilic in accordance with the property of the drug in the adhesive, and as the case may be, the part of the adhesive which is to be brought into contact with a skin may be replaced if desired by any other adhesive material that will adhere to skin. In general, conventional acrylic series or rubber series adhesive agents suitably can be used, and in addition, polysaccharide series or the like vegetable adhesive materials or gelatin or the like animal adhesive materials can be used, if desired. The thickness of this layer is suitably about 20 to 30 μm.

As the release-controlling layer (4), any well-known polymeric films or high polymeric porous films can be used, including, for example, ethylene-vinyl acetate copolymers, silicones, acrylic series resins, polyethylenes, ethyl celluloses, etc. In particular, films are preferred that are inactive when stored but that become active when in contact with the skin, in view of the object of the present invention and of the characteristics of the base polymer component in the adhesive. Specifically, these display no function as a release-controlling membrane before the adhesive is applied to the skin but can be reactivated when adhered to the skin, due to the temperature and the moisture on the skin surface, thereby to functioning to control the permeation and diffusion of the drug into the skin. In addition, the close adhesion of the adhesive to the skin is one fundamental condition necessary for the quantitative absorption of the drug into the skin, and therefore, the reactivation of the present release-controlling membrane has the additional function of increasing adhesiveness of the adhesive.

In the adhesives of the present invention, the base polymer component often acts as a matrix-controlling agent, and therefore, provides a release-retarding activity or a release-accelerating activity, as desired.

In addition, the present membrane is used in direct contact with a human skin, and therefore, it is optionally non-irritating. For this reason, a conventional gelatin membrane is preferably used in the present invention. Specific examples of gelatin membrane are set forth below. (A) A diepoxy compound as a crosslinking agent is added to a gelatin-aqueous solution and a dextran-aqueous solution. The resulting mixture is filmed and then dried. Afterwards, this is heated at 60° C. to complete crosslinking. The membrane formed is a phase-separated membrane, comprising gelatin and dextran. Next, the membrane is dipped in water to remove the dextran and then dried again to give a porous gelatin membrane having a thickness of from 10 to 30 μm. If the membrane is brittle, a cloth such as a nylon tricot made of thin fibers and having a light weight (that is, having a rough-stitched structure) can be dipped in the gelatin-dextran-crosslinking agent-aqueous solution and then processed by the same treatment to give a reinforced membrane. (B) A gelatin/water, a glycerin and a crosslinking agents are blended and then dried and crosslinked in the same manner as the above process (A), to obtain a membrane having a thickness of from 30 to 40 μm. This belongs to a liquid membrane, as containing 20 to 50% of glycerin. Because of the characteristics of the gelatin, the membrane obtained is relatively hard and gives a dry feeling, after dried at normal temperature, but this may be activated by the temperature and the moisture on the surface of a skin to be converted into a wet and adhesive membrane. When adhered to the skin, the glycerin acts to moisten the skin and maintain this condition closely adhering to the skin because of the its adhesiveness. The gelatin membrane is a fundamental structure promoting the quantitative absorption of the drug into a skin. It is considered the film (A) mainly controls the diffusion of the drug/polymer and that membrane (B) mainly retards or accelerates the diffusion of the drug.

As the liner (5), conventional release papers or release membranes can be used.

As the rigid base support (6), synthetic resin supports are preferably used, including, for example, polyesters, polypropylenes, polyethylenes, polycarbonates, polystyrenes, etc. In addition, other tabular materials can be used. The rigid base support (6) must be inert to the drug in the drug-containing layer (3) and additionally must have a suitable rigidity so that the adhesive is not broken by shock. The thickness of the base support (6) is preferably about 100 to 500 μm or so.

The shape o the adhesives of the present invention is not specifically limitative but may be any suitable shape required for application, such as a circular shape, a square shape, etc. The size and the thickness thereof may properly be determined in accordance with the strength of the drug contained, the age or condition of a patient, the desired therapeutic effect, the place to which the adhesive is applied, the intended period for the release of the drug, etc.

In actual use of the adhesives of the present invention, the diffusion, release and distribution of the drug contained are considered to occur almost as follows, although the scope of the present invention does not depend upon this theory of effectiveness and is not to be construed as limited thereby.

(1) The drug is kneaded with a molten base polymer component. (The kneading is carried out under a mild condition at a temperature which is not much higher than the melting point of the polymer.) After kneading, the drug in the drug-containing layer (3) is dissolved or dispersed in a crystalline or non-crystalline solid polymer, while stored at a normal temperature of about 30° C. or lower If the drug is dissolved in the polymer component, it is in the form of a molecular dispersion located near the segments of the amphiphilic polymer having an affinity with the drug. If the drug is clathrated or coated with a substance which is insoluble in the base polymer, this is dispersed in the polymer component.

(2) The adhesive is peeled off from the liner (5) and is applied to the skin.

(3) The amphiphilic polymer of the present invention, which constitutes the drug-containing layer (3), enters the liquid phase in contact with the surface of the skin because of the body temperature and of the heat-sensitivity of the polymer compound. When a heat-sensitive and moisture-sensitive reactivating adhesive membrane is provided on the adhesive, the film initially becomes adhesive because of the body temperature, and adheres to the skin prior to the dissolution of the polymer compound (4) Some time after the application of the adhesive to the skin, a certain amount of the moisture escaping from the surface of the skin reaches the liquid polymer in the drug-containing layer, and being to hydrate the polymer In actual practice, the melting of the polymer and its hydration proceed under an antagonistic state therebetween, and the polymer is dissolved or liquefied more easily because of melting point depression, and finally, the whole becomes a viscous liquid that flows to the side of the membrane or to the surface of the skin and thus gradually spreads thereover. The action of the polymer in controlling the flow and diffusion of a drug to the surface of the skin varies, depending upon the kind of the polymer, as referred to in the previous explanation of the water-sensitivity, depending primary on the molecular weight (melt viscosity) of the polymer and its predominantly hydrophilic or hydrophobic overall character. In addition, the action of the polymer differs, depending upon the presence or absence of a membrane over the polymer component.

In any case, the common fact is that the amphiphilic substance having both a hydrophilic part and a hydrophobic part and having a certain solubility (affinity) in water is enlarged in volume so as to minimize the contact area of the hydrophobic part with water, and the substance shows a tendency to move to the interface. That is, the substance shows a tendency to gather on a moistened skin surface and assumes a molecule-extended stage.

(5) On the surface of the skin, the drug is distributed and absorbed into the skin with an intrinsic permeation speed, whereupon the weak interaction between each segment of the amphiphilic substance and the drug, provided by its tapered structure and affinity, act to pertinently regulate the release of the drug. Accordingly, the extended state of the polymer due to its partially hydrophobic nature is advantageous for releasing a slight amount of the drug with a high efficiency.

In this step, the drug is absorbed into the skin, while the polymer is not absorbed, since the molecule of the polymer is large. In general, it is considered that molecules having a larger molecular weight of about 3,000 or more are scarcely absorbed into the skin, even when the skin is stripped with a solvent having an activity as an enhancer, such as dimethylsulfoxide (DMSO), etc. In the present invention, the block polymers which satisfy the above-mentioned condition preferably have a molecular weight of from about 2,000 to 5,000, and therefore, these are sparingly absorbed into a normal skin and are extremely safe.

Low molecular compounds, except hydrocarbons having no polar group, generally have both a polar group and a nonpolar group in the molecule and consequently a well balanced molecular structure as is often the case with the molecular structure of drugs. When a drug is used in the form of an adsorbents for percutaneous administration, it is desirable that the drug be relatively weakly bonded to a polymer which is a base component having a relatively low affinity, and be uniformly dispersed to have a high activity coefficient, to promote the release efficiency of the drug. However, the desired release pattern is to be so selected that the optimum rate of sustained release of the drug can be attained in accordance with the strength of the drug, the age and condition of the patient, the desired therapeutic effect, the place to which the adhesive is applied, the desired period of release of the drug, etc. The sustained release of the drug is affected by various factors, including the strength of the bond between the drug and the base polymer, i.e., the weak intermolecular interaction therebetween, the dispersion state of the drug in the base polymer component on the molecular level, the thermal and physico-chemical behaviors of the polymer and the drug, etc.

If the bond between the drug and the polymer is too strong, for example, such as a coordination bond, covalent bond, ionic bond, etc., it is considered that the drug reacts with the polymer and is chemically changed. In addition, a high activity coefficient cannot be attained in such case. Conversely, if these two are bonded by a weak bond such as hydrogen bond or a van der Waal's bond, the reaction of the drug is prevented and any desired high degree of activity of the drug can be obtained.

Without being found by theory, the relation between the amphiphilic alkyleneoxide segment polyurethanes for use in the present invention and drugs is considered to be as follows:

The alkyleneoxides have an ether-oxygen and the oxygen has an affinity with water, and therefore, this segment is hydrophilic, which is well known. In addition, the oxygen may form a hydrogen bond with an active hydrogen, for example, in alkylcarboxylic acids (e.g., oleic acid, etc.) which are polar hydrocarbons or in higher alcohols whereby the alkyleneoxides are solubilized, as is also well known, or in the case of drugs, where the same weak bond is formed Accordingly, percutaneous administration of a slight amount of prostagnaldins (PG's) which are extremely easily decomposed substances having a high physiological activity is possible according to the present invention. PG's are unsaturated fatty acids having a hydroxyl group and having 20 carbon atoms, which have a fairly strong polarity. These are, in general, easily soluble in polar organic solvents such as alcohols, acetone, chloroform, ethyl acetate, etc. and are largely in soluble in low polarity solvents such as hexane, petroleum ether, etc. Further, these are largely in soluble in water. PG's are structurally composed of a lipophilic part and a hydrophilic part. In view of the above-mentioned characteristics, the formation of a weak interaction between the PG's and the polyalkyleneoxide segments is likely to occur.

On the other hand, the degree of the hydrophobicity of alkyleneoxide varies, depending upon the number of the methylene carbons therein, although this hydrophobic effect is not remarkable in the monomer units, and is significant only after the formation of the polymer segments by continuously connecting the monomer units in a linear form. In addition, a smoothly tapered hydrophilicity-hydrophobicity gradient can be formed in the polymer by adjacently connecting the segments of the monomer units having increasing or decreasing numbers of methylene groups in order. After a drug is applied to the polymer to saturate the ether-oxygens of the polymer by a weak bond with the oxygen atom in the form of a molecular dispersion, a concentration gradient is formed in the dispersed state of the drug along the tapered gradient of the segments of the polymer. If a drug having a strong lipophilicity is applied to the polymer, the methylene chain effectively accomplishes the molecular dispersion of the drug and therefore, the same concentration gradient can be formed in the molecular dispersion. Such smoothly tapered hydrophilicity-hydrophobicity gradient in the polymer results in the generation of the position having an affinity of a highest concentration near the segments corresponding to the solubility constant of the drug. The polymers have both hydrophilic segments and oleophilic segments and therefore are called amphiphilic high molecular compounds. Further, these have a molecular structure that always permits a lipophilic drug applied to move in the direction of the lipophilic segments and a hydrophilic drug applied to move in the direction of the hydrophilic segments.

Although some problem may occur due to the interaction between the ester bond of a lipophilic polyester segment and a drug, the problem should be limited in extent, since the polyester is an aliphatic polyester, the segment accounts for only one block of the polynary block polymer, and the intermolecular force is weakened because of the copolymerization effect as influenced by other blocks. Because of these factors, the reactivity of the polyester segment with a drug is extremely low, and therefore the segment does not cause any practical problems.

Each segment of the polymer is blocked by the urethane bond, and each segment displays individual thermal movement, depending upon its molecular bond power, molecular weight and intermolecular force. Accordingly, the movement of the drug begins near the segments exhibiting an active thermal movement. The complete melting temperature of the polymer is determined by the interaction of the segments with each other, and the melting temperature differs in accordance with the thermal movement of each segment.

As mentioned above, the release of a variety of drugs of a broad range is made possible by the intermolecular interaction between the polymer and the drug, and the resulting sustained release process may be precisely and individually controlled.

The following examples are intended to illustrate particular embodiments of the present invention, but are not to be construed as limiting the scope of the present invention in any way.

EXAMPLE 1

A benzene solution (20 w/v%) of 1 mol of polypropylene glycol (average molecular weight 400) was reacted with a benzene solution (20 w/v%) of 2 mols of hexamethylene diisocyanate at 55° to 55° C. for 3 hours. Then, a benzene solution (20 w/v%) of a product obtained by reacting 1 mol of polytetramethylene glycol (average molecular weight 650) and 1.05 mols of n-octadecyldiisocyanate at 60° to 70° C. for 3 hours was added to the resulting reaction product, and further reacted at 50° to 55° C. for 3 hours. To the reaction product obtained was added a benzene solution (20 w/v%) of 1 mol of polyethylene glycol (average molecular weight 1,000), and still further reacted at 50° to 55° C. for 3 hours. Thereafter, the obtained was lipophilized to obtain the following polymer.

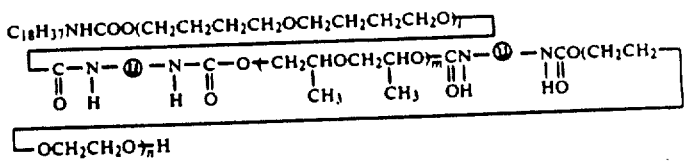

wherein the polytetramethylene glycol segment has an average molecular weight of 650;

the polypropylene glycol segment has an average molecular weight of 400;

the polyethylene glycol segment has an average molecular weight of 1,000; and

Ⓤ represents a skeleton of hexamethylene-diisocyanate.

A waxy crystalline polymer having the above structural formula was heated at 40° C. to give a transparent liquid polymer having a low viscosity, and then, prostaglandin (17S, 20-dimethyl-trans-Δ²-PGE₁) was added thereto in an amount of 0.1 wt% and well stirred. The drug having a melting point of from 97° to 100° C. completely dissolved in the polymer. This solution was coated on a release paper in a thickness of 200 μ, and was cooled at 5° C. or below so as to more completely solidify the polymer. The resulting structure was punched with a dumbbell of 1.5 cm × 1.5 cm to obtain a polymer base containing about 20 mg of the drug. Separately, a low modulus 1, 2-polybutadiene foam (foam magnification: three times, thickness: 200 μm, size: 3 cm × 3 cm) was prepared as a surface coat material, and a polyacrylate adhesive material was coated on one surface thereof in a thickness of about 30 μm. The polymer side of the previously prepared drug-containing polymer base was attached to the adhesive surface of the coat membrane. The resulting adhesive structure was put in an aluminium-plated moisture-proof membrane bag package and sealed in vacuum.

This was stored for 6 months at 25° C. or below and then removed from the bag. The stability of the drug was tested and no change was noted, indicating that the drug was stably preserved as being uniformly dissolved and solidified in the polymer crystal. No bleeding of the drug through the surface of the adhesive was noted.

The release paper was peeled off from the drug-containing polymer, which was adhered to the surface of a human skin. The polymer in contact with the skin began to change phase, as it was sensitized by the body temperature and the moisture generated from the surface of the skin. The drug-containing polymer was originally a white solid at about 30° C. or below and gradually changed to a paste at 30° C. or above and thereafter this rapidly melted as it warmed to body temperature to become a transparent liquid. However, the resulting liquid was not so fluid as to freely flow across the surface of the skin but remained viscous enough to be well-adhered to the skin.

After 48 hours of application, the amount of the drug remaining in the polymer base was determined to be 15 to 20%. Since the amount of drug remaining in a conventional percutaneous absorbents in similar circumstances is about 70 to 80%, a remarkably high efficiency in releasing the drug to a skin was adhesive for percutaneous administration of the present invention.

Next, the behavior of the drug-containing polymer in the adhesive for percutaneous administration of the present invention was observed with an optical microscope. The white polymer was observed to rapidly melt at about 36° C. or so, which is approximately body temperature, to become a transparent liquid. After water was added thereto in an amount of 1 to 2 mg/cm²·hr, which approximates the expected amount of human sweat, the polymer was found to form a large number of microspheres in the interface with water, which were vigorously drawn into the aqueous phase and dispersed therein, confirming the self-dispersion of the liquid polymer owing to the interface energy, after the polymer formed on a weak bond with the drug present, and the same phenomenon would be expected to occur on the surface of the skin.

In the microspheres, the hydrophilic polymer segments are considered to be directed to the water interface. In contact with the skin, the microspheres would be expected to break due to the lipids present on the surface of the skin, resulting in a phase conversion whereby the present drug, which is a water-insoluble good lipid having a large distribution coefficient, would have gradually been absorbed through the corneum of the skin.

EXAMPLE 2

The following polymer was prepared in the same procedure as in Example 1.

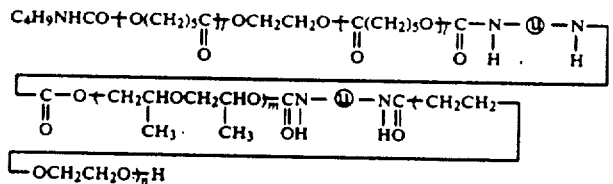

wherein the poly-ε-caprolactone segment has an average molecular weight of 530;

the polypropylene glycol segment has an average molecular weight of 400;

the polyethylene glycol segment has an average molecular weight of 1,000; and

Ⓤ represents a skeleton of hexamethylene-diisocyanate.

The polymer having the above structural formula had a melting point of 36° to 37° C., as visually measured 100 mg of the polymer was melted in the same manner as Example 1, and 3.333 mg of the α-CD-clathrated 17S,20-dimethyl-trans-Δ²-PGE₁ (α-CD being α-cyclodextrin) was blended and dispersed therein. The resulting drug-containing polymer base was sealed in vacuum and stored in a cold dark place at 25° C. or below for 6 months, and at the end of this period, no noticeable change was noted. An adhesive structure was prepared and adhered to the surface of human skin in the same manner as Example 1, and after 72 hours, the amount of the drug remaining in the polymer base was 20 to 30%, which indicates that the drug was transdermally administered in a highly efficient manner in comparison with conventional materials.

In order to regulate the release pattern of the drug, the surface of the polymer component was covered with a porous membrane of a phase-separated cross-linked gelatin-dextran as reinforced with a nylon tricot cloth in the form of a mesh (15 μm thick). This was similarly adhered to human skin, and the percentage of the drug remaining was 30 to 40% after 72 hours, indicating that the release pattern still had a relatively uniform gradient although the release percentage somewhat lowered.

EXAMPLE 3

The following polymer was produced in the same procedure as in Example 1.

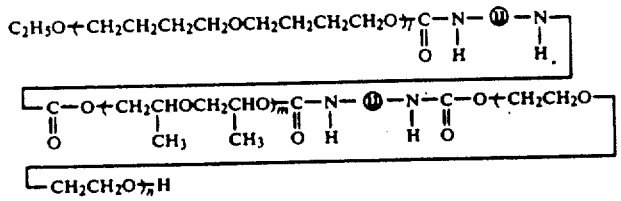

wherein the polytetramethylene glycol segment has an average molecular weight of 650;
the polypropylene glycol segment has an average molecular weight of 400;
the polyethylene glycol segment has an average molecular weight of 1,000; and
ⓤ represents a skeleton of tetramethylene-diisocyanate.

A waxy crystalline polymer having the above structural formula was heated to 40° C. to give a transparent liquid polymer having a low viscosity, and then, the drug prostaglandin E -methyl ester (PEG$_1$-methyl ester) was added thereto and well stirred. The drug was liquid and easily dissolved. After being cooled and solidified, the resulting drug-containing polymer was used as a drug-containing layer in preparation having the structure shown in FIG. 3, in which the amount of the PEG$_1$-methyl ester, the amount of the base component and the area of the drug-containing layer were 10 μg, 20 mg and 4 cm$^2$, respectively, per patch. As a release-controlling film, a reactivated gelatin film prepared as mentioned below was used.

A composition comprising:

| | |
|---|---|
| alkali gelatin | 100 parts by weight. |
| crosslinking agent (glycerol-polyglycidyl ether) | 3 parts by weight. |
| glycerin | 40 parts by weight. |
| water | 100 parts by weight. | was filmed and then dried at normal temperature. Afterwards, this was crosslinked at 60° C. for 72 hours to obtain a dry membrane having a thickness of 40 μm.

The adhesive thus formed was adhered to human skin, and after 72 hours, the percentage of drug released was measured to be 50 to 55%.

EXAMPLE 4

The following polymer was prepared in the same procedure as in Example 1.

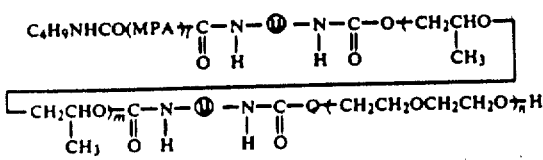

wherein MPA represents a polyester of 3-methylpentane-1, 5diol and adipic acid, and this segment has an average molecular weight of 1,000;
the polypropylene glycol segment has an average molecular weight of 750;
the polyethylene glycol segment has an average molecular weight of 1,000; and
ⓤ represents a skeleton of hexamethylene-diisocyanate.

The visual melting point of the solid polymer having the above structural formula was about 35° C. On heating, the polymer became a transparent liquid having a low viscosity. This was heated at 40° to 50° C. and the drug testosterone was added thereto in an amount of 0.5 wt% and well stirred. The drug has a melting point of 153° to 157° C. The observation of the resulting mixture with a microscope indicated the complete dissolution of the drug therein. Then, this was cooled and solidified, and the resulting solid drug-containing polymer was used as the drug-containing layer in an adhesive having the structure shown in FIG. 4, in which the amount of the testosterone, the amount of the base component and the area of the drug-containing layer were 100 μg, 20 mg and 4 cm$^2$, respectively, per patch.

The adhesive thus formed was adhered to human skin, and after 48 hours, the percentage of the drug released was measured to be about 35° to 40%, which is a relatively high value.

EXAMPLE 5

The same adhesive (OP-1206/α-CD patch) as in Example 2, containing the drug in an amount of 1 mg/kg as OP-1206 was adhered to the skin of hypertensive SHR rats, and the blood pressure depression of the rat was determined as shown in FIG. 5.

Under the same condition, a conventional PEG ointment was applied to the rats' skin. In this case, the effect was not sustained although blood pressure depression was noted in the initial stage. In comparison, the effect of the adhesive of the present Example 2 persisted for 24 hours or more, confirming the superiority of the sustained release property of the adhesive of the present invention.

As explained in detail above, the adhesives of the present invention have a heat-sensitive and water-sensitive amphiphilic polymeric compound as the base component of the drug-containing layer whereby a controlled release and distribution of a drug is possible with high safety and high efficiency for a long period of time.

More precisely, the present polymeric compound is a heat-sensitive polymeric substance which is stably solid at normal temperature and which melts at a skin surface temperature to body temperature (i.e., in a range of about 30 to 37° C.). Accordingly, the present polymer remains solid at storage temperatures, and the drug is dissolved or dispersed in the crystalline or non-crystalline polymer to permit the drug to be stored stably therein without being released or diffused into other layers. Only after the adhesive has been applied to the skin, does the drug begin to be released. Therefore, the adhesives of the present invention are free from any excess release of the drug immediately after application and the initial release can properly be controlled. In addition, since the base polymer comprises an amphiphilic polymeric compound, a variety of liquid or solid, or oleophilic or hydrophilic drugs of a broad range can be dissolved in the base polymer component. Accordingly, the present invention provides a universal percutaneous administration system which can be adapted to various drugs of widely differing chemical and therapeutic nature, as illustrated in the examples provided. In particular, the system of the present invention is suitable for percutaneous administration of highly active physiological substances which are extremely easily decomposed by heat or water and which are unstable (for example, prostaglandins). Specifically, the present invention permits even a slight amount of a drug of a highly active physiological substance to be dissolved or dispersed in the base polymer uniformly at the molecular level, because of the action of the polymer blocks having a high affinity to the drug, and the drug to be gradually released with high availability. In addition, the base polymer is extremely non-irritating in nature and so any harmful side effects can be reduced to the minimum limit. According to the specific system provided by the adhesive of the present invention, the molecular level interaction between the polymer and a drug can properly be controlled, and in addition, the sustained release of a drug can freely be controlled by the provision of a pertinent control membrane on the adhesives.

While the invention has been described in detail and with reference to specific embodiments thereof, it will be apparent to one skilled in the art that various changes and modifications can be made therein without departing from the spirit and scope thereof.

What is claimed is:

1. An adhesive for percutaneous administration, comprising a layer containing a heat-sensitive and water-sensitive amphiphilic polymer and a biologically active agent, wherein said heat-sensitive and water-sensitive amphiphilic polymer is a multi-block copolymer comprising a reaction product of an alkyleneoxide-polyether-polyol, an aliphatic polyester-polyol or an aliphatic polyether-polyol and a diisocyanate, wherein said multi-block copolymer is represented by the following general formula (A):

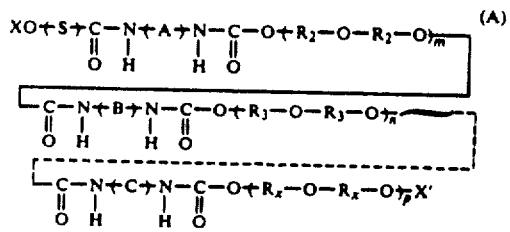

wherein (S) is selected from the group consisting of:
(a) a polyalkylene segment represented by the following general formula (I):

$$+R_1-O-_1-O+_{\overline{l}}$$ (I)

wherein $R_1$ to $R_x$ each represents an alkylene group having from 7 to 2 carbons, the number of carbon atoms in each group of the series $R_1$ to $R_x$ being less than the number of carbon atoms in the previous alkylene groups of the series from $R_1$ to $R_x$, provided that the number of carbon atoms in any two immediately adjacent members of the series $R_1$ to $R_x$ may be equal, and any alkyleneoxide group containing said alkylene group of the series from $R_1$ to $R_x$ may be omitted;

(b) an aliphatic polyester segment which is the reaction product of a dibasic acid and a dihydric alcohol represented by the following general formula (II):

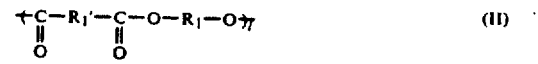

wherein $R_1$ and $R_1'$, which may the same or different, each represents an alkylene group, $R_1$ represents an alkylene group of dihydric alcohol, the total number of carbon atoms in $R_1$ and $R_1'$ is greater than the number of carbon atoms in $R_2$, $R_2$ to $R_x$ each represents an alkylene group having from 4 to 2 carbon atoms, the number of carbon atoms in each group of the series $R_2$ to $R_x$ being less than the number of carbon atoms in the previous alkylene groups of the series from $R_2$ to $R_x$, provided that the number of carbon atoms in any two immediately adjacent members of the series $R_2$ to $R_x$ may be equal, and any alkyleneoxide group containing said alkylene group of the series from $R_2$ to $R_x$ may be omitted; and (c) a polyester segment which is the reaction product of a ring-cleaved polymer of a cyclic ester and a dihydric alcohol represented by the following general formula (III):

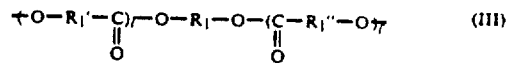

wherein $R_1'$ and $R_1''$, which may be the same or different, each represents a reaction of a ring-cleaved polymer of a cyclic ester containing 5 carbon atoms, $R_1$ represents an alkylene group of said dihydric alcohol, $R_2$ to $R_x$ each represents an alkylene group having from 4 to 2 carbon atoms, the number of carbon atoms in each group of the series $R_2$ to $R_x$ being less than the number of carbon atoms in the previous alkylene groups of the series from $R_2$ to $R_x$, provided that the number of carbon atoms in any two immediately adjacent members of the series $R_2$ to $R_x$ may be equal, and any alkyleneoxide group containing said alkylene group of the series from $R_2$ to $R_x$ may be omitted; and in general formula (A), —OX represents a group selected from the group consisting of RO—, RCOO—,

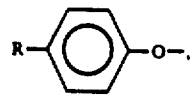

, R—NHCOO—, and ROOCHN—⑪—NHCOO—, wherein R represents an alkyl group having 1 to 18 carbon atoms or a vinyl group and ⑪ represents an isocyanate skeleton group; —OX' represents a group selected from the group consisting of —OH, —OCl, —OBr and —OF; l, l', m, n and p, which may be the same or different, each is a positive integer; and (A), (B)

and (C), which may be the same or different, each represents an isocyanate skeleton group.

2. An adhesive as claimed in claim 1, wherein said amphiphilic polymer has a melting point of from about 30° to 37° C.

3. An adhesive as claimed in claim 1, wherein said polyalkyleneoxide segment represented by formula (I) is selected from the group consisting of polyethylene glycol, polypropylene glycol, polytetramethylene glycol, polypentamethylene glycol, polyhexamethylene glycol and polyheptamethylene glycol; in said aliphatic polyester segment represented by formula (II), the total number of carbon atoms in $R_1$ and $R_1'$ is at least 5; said polyester segment represented by formula (III) is a reaction product of a poly-$\epsilon$-caprolactone or poly-$\beta$-methyl-$\delta$-valerolactone and an alkylene glycol; and said aliphatic polyester segment represented by formula (II) and said polyester segment represented by formula (III) each further comprises a polyalkylene oxide moiety that is selected from the group consisting of polyethylene glycol, polypropylene glycol and polytetramethylene glycol.

4. An adhesive as claimed in claim 3, wherein (S) represents an lipophilic or hydrophobic group.

5. An adhesive as claimed in claim 1, wherein said biologically active agent is a prostaglandin.

6. An adhesive as claimed in claim 5, wherein said prostaglandin is 17S, 20- dimethyl-trans-$\Delta^2$-PGE$_1$, a methyl ester thereof or a cyclodextrin-clathrate compound thereof.

7. An adhesive as claimed in claim 1, which further comprises a surface coat layer on the layer containing the heat-sensitive and water-sensitive amphiphilic polymer and biologically active agent, a pressure-sensitive adhesive layer and a liner, said surface coat layer being bonded to said layer containing the heat-sensitive and water-sensitive amphiphilic polymer and biologically active agent by said pressure-sensitive adhesive.

8. An adhesive as claimed in claim 7, wherein said surface coat layer comprises 1, 2-polybutadiene foam.

9. An adhesive as claimed in claim 1, which further comprises a release-control layer.

10. An adhesive as claimed in claim 9, wherein said release-control layer is a heat-sensitive and moisture-sensitive reactivating adhesive membrane.

11. An adhesive as claimed in claim 10, wherein said reactivating adhesive membrane is a gelatin membrane.

12. A method of administering a biological agent comprising the steps of:
(1) incorporating said agent in a layer comprising a heat-sensitive and water sensitive amphiphilic polymer, and
(2) bringing said layer in sufficient contact with the skin of a subject to permit transdermal transfer of said agent,
wherein said amphiphilic polymer is a multi-block copolymer comprising a reaction product of an alkyleneoxide-polyetherpolyol, an aliphatic polyester-polyol or an aliphatic polyetherpolyol and a diisocyanate, and wherein said multi-block copolymer is represented by the following general formula (A):

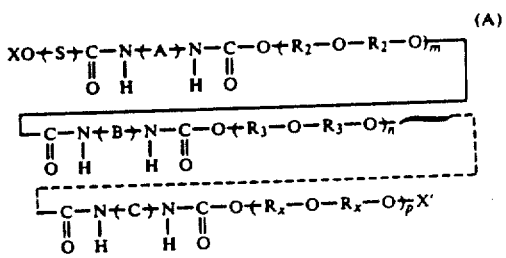

wherein (S) is selected from the group consisting of:
(a) a polyalkylene segment represented by the following general formula (I):

$$+R_1-O-R_1-O+_l \qquad (I)$$

wherein $R_1$ to $R_x$ each represents an alkylene group having from 7 to 2 carbons, the number of carbon atoms in each group of the series $R_1$ to $R_x$ being less than the number of carbon atoms in the previous alkylene groups of the series from $R_1$ to $R_x$, provided that the number of carbon atoms in any two immediately adjacent members of the series $R_1$ to $R_x$ may be equal, and any alkyleneoxide group containing said alkylene group of the series from $R_1$ to $R_x$ may be omitted;
(b) an aliphatic polyester segment which is the reaction product of a dibasic acid and a dihydric alcohol represented by the following general formula (II):

$$+C-R_1'-C-O-R_1-O+_n \qquad (II)$$
$$\phantom{+}\|\phantom{-R_1'-}\|$$
$$\phantom{+}O\phantom{-R_1'-}O$$

wherein $R_1$ and $R_1'$, which may be the same or different, each represents an alkylene group, $R_1$ represents an alkylene group of dihydric alcohol, the total number of carbon atoms in $R_1$ and $R_1'$ is greater than the number of carbon atoms in $R_2$, $R_2$ to $R_x$ each represents an alkylene group having from 4 to 2 carbon atoms, the number of carbon atoms in each group of the series $R_2$ to $R_x$ being less than the number of carbon atoms in the previous alkylene groups of the series from $R_2$ to $R_x$, provided that the number of carbon atoms in any two immediately adjacent members of the series $R_2$ to $R_x$ may be equal, and any alkyleneoxide group containing said alkylene group of the series from $R_2$ to $R_x$ may be omitted; and
(c) a polyester segment which is the reaction product of a ring-cleaved polymer of a cyclic ester and a dihydric alcohol represented by the following general formula (III):

$$+O-R_1'-C)_r-O-R_1-O-(C-R_1''-O+_p. \qquad (III)$$
$$\phantom{+O-R_1'-}\|\phantom{-O-R_1-O-}\|$$
$$\phantom{+O-R_1'-}O\phantom{-O-R_1-O-}O$$

wherein $R_1'$ and $R_1''$, which may be the same or different, each represents a reaction of a ring-cleaved polymer of a cyclic ester containing $m$ carbon atoms, $R_1$ represents an alkylene group of said dihydric alcohol, $R_2$ to $R_x$ each represents an alkylene group having from 4 to 2 carbon atoms, the number of carbon atoms in each group of the series $R_2$ to $R_x$ being less than the number of carbon atoms in the previous alkylene groups of the series from $R_2$ to $R_x$, provided that the number of carbon atoms in any two immediately adjacent members of the series $R_2$ to $R_x$ may be equal, and any alkyleneoxide group containing said alkylene group of the series from $R_2$ to $R_x$ may be omitted; and in general formula (A), —OX represents a group selected from the group consisting of RO—, RCOO—,

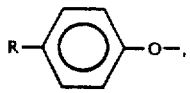

R—NHCOO—, and ROOCHN—Ⓟ—CHCOO—, wherein R represents an alkyl group having 1 to 18 carbon atoms or a vinyl group and Ⓟ represents an isocyanate skeleton group; —OX' represents a group selected from the group consisting of —OH, —OCl, —OBr and —OF; l, l', m, n and p, which may be the same or different, each is a positive integer, and (A), (B) and (C), which may be the same or different, each represents an isocyanate skeleton group.

13. A process for producing an adhesive for percutaneous administration which comprises kneading uniformly a heat-sensitive and water-sensitive amphiphilic polymer and a biologically active agent at a temperature higher than the melting point of said polymer and then applying the resulting mixture on the surface of a support, wherein said amphiphilic polymer is a multi-block copolymer comprising a reaction product of an alkyleneoxide-polyether-polyol, an aliphatic polyester-polyol or an aliphatic polyether-polyol and a diisocyanate, and wherein said multi-block copolymer is represented by the following general formula (A):

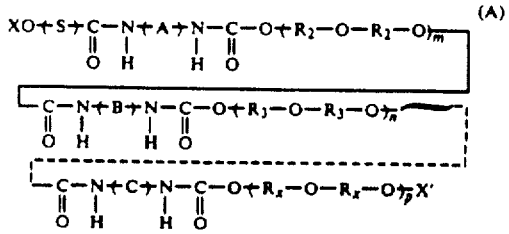

wherein (S) is selected from the group consisting of:
(a) a polyalkylene segment represented by the following general formula (I):

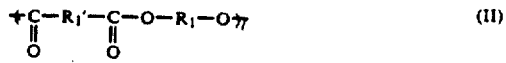     (I)

wherein $R_1$ to $R_x$ each represents an alkylene group having from 7 to 2 carbons, the number of carbon atoms in each group of the series $R_1$ to $R_x$ being less than the number of carbon atoms in the previous alkylene groups of the series from $R_1$ to $R_x$, provided that the number of carbon atoms in any two immediately adjacent members of the series $R_1$ to $R_x$ may be equal, and any alkyleneoxide group containing said alkylene group of the series from $R_1$ to $R_x$ may be omitted;

(b) an aliphatic polyester segment which is the reaction product of a dibasic acid and a dihydric alcohol represented by the following general formula (II):

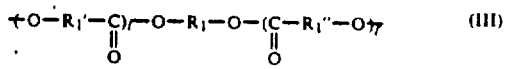     (II)

wherein $R_1$ and $R_1'$, which may be the same or different, each represents an alkylene group, $R_1$ represents an alkylene group of dihydric alcohol, the total number of carbon atoms in $R_1$ and $R_1'$ is greater than the number of carbon atoms in $R_2$, $R_2$ to $R_x$ each represents an alkylene group having from 4 to 2 carbon atoms, the number of carbon atoms in each group of the series $R_2$ to $R_x$ being less than the number of carbon atoms in the previous alkylene groups of the series from $R_2$ to $R_x$, provided that the number of carbon atoms in any two immediately adjacent members of the series $R_2$ to $R_x$ may be equal, and any alkyleneoxide group containing said alkylene group of the series from $R_2$ to $R_x$ may be omitted; and (c) a polyester segment which is the reaction product of a ring-cleaved polymer of a cyclic ester and a dihydric alcohol represented by the following general formula (III):

$$+O-R_1'-\underset{\underset{O}{\|}}{C})-O-R_1-O-(\underset{\underset{O}{\|}}{C}-R_1''-O\!\!\not\!\!\,_{\overline{\eta}}\quad (III)$$

wherein $R_1'$ and $R_1''$, which may be the same or different, each represents a reaction of a ring-cleaved polymer of a cyclic ester containing 5 carbon atoms, $R_1$ represents an alkylene group of said dihydric alcohol, $R_2$ to $R_x$ each represents an alkylene group having from 4 to 2 carbon atoms, the number of carbon atoms in each group of the series $R_2$ to $R_x$ being less than the number of carbon atoms in the previous alkylene groups of the series from $R_2$ to $R_x$, provided that the number of carbon atoms in any two immediately adjacent members of the series $R_2$ to $R_x$ may be equal, and any alkyleneoxide group containing said alkylene group of the series from $R_2$ to $R_x$ may be omitted; and in general formula (A), —OX represents a group selected from the group consisting of RO—, RCOO—,

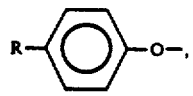

, R—NHCOO—, and ROOCHN—Ⓟ—NHCOO—, wherein R represents an alkyl group having 1 to 18 carbon atoms or a vinyl group and Ⓟ represents an isocyanate skeleton group; —OX' represents a group selected from the group consisting of —OH, —OCl, —OBr and —OF; l, l', m, n and p, which may be the same or different, each is a positive integer; and (A), (B) and (C), which may be the same or different, each represents an isocanate skeleton group.

* * * * *